United States Patent
Wickenden et al.

(10) Patent No.: US 6,326,385 B1
(45) Date of Patent: Dec. 4, 2001

(54) METHODS FOR TREATING OR PREVENTING PAIN

(75) Inventors: Alan David Wickenden, Cary; Gregory Cooksey Rigdon, Durham; Grant Andrew McNaughton-Smith, Morrisville; Michael Francis Gross, Durham, all of NC (US)

(73) Assignee: ICAgen, Inc., Durham, NC (US)

(*) Notice: Subject to any disclaimer, the term of this patent is extended or adjusted under 35 U.S.C. 154(b) by 0 days.

(21) Appl. No.: 09/631,747

(22) Filed: Aug. 4, 2000

Related U.S. Application Data

(60) Provisional application No. 60/147,221, filed on Aug. 4, 1999, provisional application No. 60/158,712, filed on Oct. 8, 1999, and provisional application No. 60/165,847, filed on Jan. 16, 1999.

(51) Int. Cl.[7] .......................... A61K 31/44; A61K 31/535
(52) U.S. Cl. ...................... 514/352; 514/233.5; 514/332; 514/336; 514/337; 514/338; 514/339; 514/340
(58) Field of Search .................................. 514/352, 233.5, 514/332, 336, 337, 338, 339, 340

(56) References Cited

U.S. PATENT DOCUMENTS

| | | |
|---|---|---|
| 4,845,107 | 7/1989 | Baker et al. . |
| 5,340,827 | 8/1994 | Beeley et al. . |
| 5,859,032 | 1/1999 | Nishino et al. . |
| 5,958,944 | 9/1999 | Arita et al. . |

FOREIGN PATENT DOCUMENTS

| | | |
|---|---|---|
| WO 98/37068 | 8/1998 | (WO) . |
| WO 99/07832 | 2/1999 | (WO) . |
| WO 99/31232 | 6/1999 | (WO) . |

OTHER PUBLICATIONS

Biervert, Christian, et al. "A Potassium Channel Mutation in Neonatal Human Epilepsy," *Science* 279:403–405 (Jan. 16, 1998).

Kubisch, Christian, et al. "KCNQ4, a Novel Potassium Channel Expressed in Sensory Outer Hair Cells, Is Mutated in Dominant Deafness," *Cell* 96:437–446 (Feb. 5, 1999).

Leppert, Mark, et al. "Benign familial neonatal convulsions linked to genetic markers on chromosome 20," *Nature*, 337:647–648 (Feb. 16, 1989).

Wang, Hong–Sheng, et al. "KCNQ2 and KCNQ3 Potassium Channel Subunits: Molecular Correlates of the M–Channel," *Science* 282:1890–1893 (Dec. 4, 1998).

Yang, Wen–Pin, et al. "Functional Expression of Two KvLQT1–related Potassium Channels Responsible for an Inherited Idiopathic Epilepsy," *The Journal of Biological Chemistry* 273(31):19419–19423 (1998).

*Primary Examiner*—William R. A. Jarvis
(74) *Attorney, Agent, or Firm*—Townsend and Townsend and Crew LLP; Annette S. Parent

(57) ABSTRACT

The present invention relates to a novel method of treating of pain, using compounds that modulate KCNQ potassium channels and currents.

31 Claims, 12 Drawing Sheets

(33)

(34)

(35)

(36)

(37)

(38)

(39)

(40)

(41)

(42)

(43)

(44)

(45)

(46)

(47)

METHODS FOR TREATING OR PREVENTING PAIN

CROSS-REFERENCES TO RELATED APPLICATIONS

This application claims priority to USSN 60/147,221, filed Aug. 4, 1999, USSN 60/158,712, filed Oct. 8, 1999, and USSN 60/165,847, Nov. 16, 1999, herein each incorporated by reference in their entirety. This application is related to USSN 09/632,576, filed Aug. 4, 2000, Townsend and Townsend Attorney docket number 018512-003810US, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Ion channels are cellular proteins that regulate the flow of ions, including calcium, potassium, sodium and chloride, into and out of cells. These channels are present in all human cells and affect such processes as nerve transmission, muscle contraction and cellular secretion. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels have now been associated with a number of physiological processes, including regulation of heartbeat, dilation of arteries, release of insulin, excitability of nerve cells, and regulation of renal electrolyte transport.

Potassium channels are made by alpha subunits that fall into at least 8 families, based on predicted structural and functional similarities (Wei et al., *Neuropharmacology* 35(7):805–829 (1997)). Three of these families (Kv, eag-related, and KQT) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels, or BK channels, have seven transmembrane domains (Meera et al., *Proc. Natl. Acad. Sci. U.S.A.* 94(25):14066–71 (1997)) and are gated by both voltage and calcium or pH (Schreiber et al., *J. Biol. Chem.* 273:3509–16 (1998)). Another family, the inward rectifier potassium channels (Kir), belong to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KQT family beta subunit, minK, primarily changes activation kinetics (Sanguinetti et al., *Nature* 384:80–83 (1996)).

Slo or BK potassium channels are large conductance potassium channels found in a wide variety of tissues, both in the central nervous system and periphery. They play a key role in the regulation of processes such as neuronal integration, muscular contraction and hormone secretion. They may also be involved in processes such as lymphocyte differentiation and cell proliferation, spermatocyte differentiation and sperm motility. Three alpha subunits of the Slo family have been cloned, i.e., Slo1, Slo2, and Slo3 (Butler et al., *Science* 261:221–224 (1993); Schreiber et al., *J. Biol. Chem.*, 273:3509–16 (1998); and Joiner et al., *Nature Neurosci.* 1: 462–469 (1998)). These Slo family members have been shown to be voltage and/or calcium gated, and/or regulated by intracellular pH.

Certain members of the Kv family of potassium channels were recently renamed (see Biervert et al., *Science* 279:403–406 (1998)). KvLQT1 was re-named KCNQ1, and the KvLQT1-related channels (KvLR1 and KvLR2) were renamed KCNQ2 and KCNQ3, respectively. More recently, a fourth member of the KCNQ subfamily was identified (KCNQ4) as a channel expressed in sensory outer hair cells (Kubisch et al., *Cell* 96(3):437–446 (1999)).

KCNQ2 and KCNQ3 have been shown to be nervous system-specific potassium channels associated with benign familial neonatal convulsions ("BFNC"), a class of idiopathic generalized epilepsy (see Leppert et al., *Nature* 337:647–648 (1989); Yang et al., *J. Biol. Chem.* 273:19419–19423 (1998)). These channels have been linked to M-current channels (see Wang et al., *Science* 282:1890–1893 (1998)). The discovery and characterization of these channels and currents provides useful insights the physiologic and pathophysiologic roles of KCNQ-based currents. In addition, this discovery provides useful insights into how these voltage dependent (Kv) potassium channels function in different environments, and how they respond to various activation mechanisms.

In the present invention, we show, for the first time, that KCNQ2/3 channels and currents are expressed in dorsal root ganglion cells, indicating a possible role for these currents in pain processing. Furthermore, we show that a selective opener of KCNQ channels is analgesic in animal models of pain, and an anxiolytic in animal models of anxiety. The use of KCNQ channels as molecular targets for drugs to treat pain and anxiety, and the use of KCNQ modulators for the treatment of pain and anxiety is the subject of the present invention.

SUMMARY OF THE INVENTION

The present invention relates to novel compounds and the use of such compounds in methods of treating pain and anxiety, by increasing ion flow in KCNQ channels and activating KCNQ currents by opening the channels.

In one aspect, the present invention relates to a method for reducing pain in a subject in need thereof by increasing ion flow through KCNQ potassium channels in a cell, the method comprising the step of administering to the subject a pharmaceutical composition comprising a pharmaceutically acceptable carrier and a compound able to increase ion flow through KCNQ potassium channels, said composition administered to the subject in a potassium channel-opening amount, thereby reducing pain in the subject.

In another aspect, the present invention relates to a method for reducing anxiety in a subject in need thereof by increasing ion flow through KCNQ potassium channels in a cell, the method comprising the step of administering to the subject a pharmaceutical composition comprising a pharmaceutically acceptable carrier and a compound able to increase ion flow through KCNQ potassium channels, said composition administered to the subject in a potassium channel-opening amount, thereby reducing anxiety in the subject.

In one embodiment, the potassium channel-opening amount is 0.1 mg/kg to 200 mg/kg. In another embodiment, the potassium-channel opening amount is 1 mg/kg to 150 mg/kg In another embodiment, the potassium channel-opening amount is 10 mg/kg to 100 mg/kg.

In one embodiment, the composition is administered orally, by injection, or after surgery.

In one embodiment, the pain is somatic pain, e.g., visceral pain or cutaneous pain, or pain caused by a burn, a bruise, an abrasion, a laceration, a broken bone, a torn ligament, a torn tendon, a torn muscle, a viral infection, a bacterial infection, a protozoal infection, a fungal infection, contact dermatitis, inflammation, or cancer. In another embodiment, the inflammation is caused by trauma, infection, surgery, burns, or diseases with an inflammatory component.

In one embodiment, the pain is neuropathic, e.g., caused by injury to the central or peripheral nervous system due to cancer, HIV infection, tissue trauma, infection, autoimmune disease, diabetes, arthritis, diabetic neuropathy, trigeminal neuralgia or drug administration.

In one embodiment, the anxiety is caused by panic disorder, generalized anxiety disorder, or stress disorder, e.g., acute or post-traumatic stress disorder.

In one embodiment, the subject is a human.

In one embodiment, the KCNQ channel is a homomeric channel. In another embodiment, the KCNQ channel is a heteromeric channel. In another embodiment, the heteromeric KCNQ channel comprises a KCNQ2 polypeptide subunit. In another embodiment, the heteromeric KCNQ channel comprises a KCNQ3 polypeptide subunit. In another embodiment, the KCNQ channel is KCNQ2/3.

In one aspect, the compound able to increase ion flow through KCNQ potassium channels has the formula:

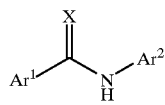

wherein
Ar$^1$ and Ar$^2$ are each members independently selected from the group consisting of aryl, substituted aryl, heteroaryl and substituted heteroaryl; and
X is a member selected from the group consisting of O, S and N—R$^1$,
wherein R$^1$ is a member selected from the group consisting of H, (C$_1$–C$_8$)alkyl, substituted (C$_1$–C$_8$) alkyl, aryl, substituted aryl, heteroaryl, substituted heteroaryl, aryl(C$_1$–C$_4$)alkyl, substituted aryl (C$_1$–C$_4$)alkyl, CN, —C(O)R$^2$, —OR$^3$, —C(O)NR$^3$R$^4$, and —S(O)$_2$NR$^3$R$^4$;

wherein R$^2$ is a member selected from the group consisting of (C$_1$–C$_8$)alkyl, substituted (C$_1$–C$_8$) alkyl, aryl, substituted aryl, heteroaryl, substituted heteroaryl, aryl(C$_1$–C$_4$)alkyl and substituted aryl (C$_1$–C$_4$)alkyl; and
R$^3$ and R$^4$ are each members independently selected from the group consisting of hydrogen, (C$_1$–C$_8$)alkyl, substituted (C$_1$–C$_8$)alkyl, aryl, substituted aryl, heteroaryl, substituted heteroaryl, aryl(C$_1$–C$_4$)alkyl and substituted aryl(C$_1$–C$_4$)alkyl, or R$^3$ and R$^4$ can be combined with the nitrogen to which each is attached to form a 5-, 6- or 7-membered ring optionally having additional heteroatoms at the ring vertices.

In another aspect, the present invention provides a compound able to increase ion flow though KCNQ potassium channels having the formula:

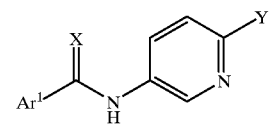

wherein,
Ar$^1$ is a member selected from the group consisting of aryl, substituted aryl, heteroaryl and substituted heteroaryl;
X is a member selected from the group consisting of O, S and N—R$^1$,
wherein, R$^1$ is a member selected from the group consisting of H, (C$_1$–C$_8$)alkyl, substituted (C$_1$–C$_8$) alkyl, heteroalkyl, substituted heteroalkyl, aryl, substituted aryl, heteroaryl, substituted heteroaryl, aryl (C$_1$–C$_4$)alkyl, substituted aryl(C$_1$–C$_4$)alkyl, CN, —C(O)R$^2$, —OR$^3$, —C(O)NR$^3$R$^4$, and —S(O)$_2$NR$^3$R$^4$;
wherein, R$^2$ is a member selected from the group consisting of (C$_1$–C$_8$)alkyl, substituted (C$_1$–C$_8$) alkyl, cycloalkyl, substituted cycloalkyl, heteroalkyl, substituted heteroalkyl, heterocyclyl, substituted heterocyclyl, alkaryl, substituted aryl, heteroaryl, substituted heteroaryl, aryl(C$_1$–C$_4$)alkyl and substituted aryl(C$_1$–C$_4$)alkyl;
R$^3$ and R$^4$ are each members independently selected from the group consisting of hydrogen, (C$_1$–C$_8$)alkyl, substituted (C$_1$–C$_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl(C$_1$–C$_4$) alkyl and substituted aryl(C$_1$–C$_4$)alkyl, or R$^3$ and R$^4$ can be combined with the nitrogen to which each is attached to form a 5-, 6- or 7-membered ring optionally having additional heteroatoms at the ring vertices; and
Y is a member selected from the group consisting of halogen, C$_1$–C$_4$ alkyl, C$_1$–C$_4$ substituted alkyl, —OCH$_3$ and —OCF$_3$.

In one embodiment, Ar$^1$ of the compound is substituted phenyl. In another embodiment, Ar$^1$ is a member selected from the group consisting of phenyl, substituted phenyl, indolyl, substituted indolyl, benzofuranyl, substituted benzofuranyl, furanyl, substituted furanyl, thienyl, substituted thienyl, isothiazolyl, substituted isothiazolyl, pyrazolyl and substituted pyrazolyl. In another embodiment, Ar$^1$ is substituted phenyl, substituted or unsubstituted 2-indolyl and substituted or unsubstituted 2-thienyl. In another embodiment, X is O. In another embodiment, the Ar$^1$ substituents are selected from the group consisting of halogen, alkyl, halo($C_1$–$C_4$)alkyl, ($C_1$–$C_4$)alkoxy, halo ($C_1$–$C_4$)alkoxy, nitro, cyano, —NHC(O)$R^7$, —NH$R^7$, phenyl and substituted phenyl, wherein $R^7$ is a member selected from hydrogen, ($C_1$–$C_8$)alkyl, substituted ($C_1$–$C_8$)alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl($C_1$–$C_4$) alkyl and substituted aryl($C_1$–$C_4$)alkyl, or $R^7$ can be combined with the nitrogen to which it is attached to form a 5-, 6- or 7-membered ring optionally having additional heteroatoms at the ring vertices.

In another embodiment, $Ar^2$ of the compound is selected from the group consisting of heteroaryl and substituted heteroaryl. In another embodiment, $Ar^2$ of the compound is pyridyl or substituted pyridyl, e.g., 6-methyl-3-pyridyl and 2-chloro-5-pyridyl. In another embodiment, $Ar^1$ of the compound is substituted aryl; $Ar^2$ is eteroaryl or substituted heteroaryl; and X is O.

In another embodiment, the compound has the formula:

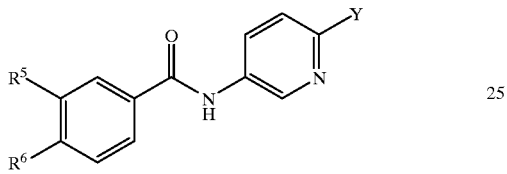

wherein, $R^5$ and $R^6$ are members independently selected from the group consisting of H, halogen, alkyl, halo ($C_1$–$C_4$)alkyl, nitro, cyano and phenyl, with the proviso that both $R^5$ and $R^6$ are not H.

In another embodiment, $R^5$ and $R^6$ are members independently selected from the group consisting of H, F, and Cl, with the proviso that both $R^5$ and $R^6$ are not H.

In another aspect, the present invention provides a compound able to increase ion flow through KCNQ potassium channels having the formula:

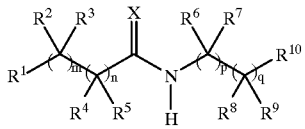

wherein $R^1$ is a member selected from the group consisting of substituted or unsubstituted branched ($C_3$–$C_8$)alkyl, substituted or unsubstituted ($C_3$–$C_8$)cycloalkyl, substituted or unsubstituted ($C_3$–$C_8$)heterocycloalkyl, substituted or unsubstituted aryl and substituted or unsubstituted heteroaryl;

$R^2$, $R^3$, $R^4$ and $R^5$ are each members independently selected from the group consisting of hydrogen, fluorine and substituted or unsubstituted ($C_1$–$C_8$)alkyl, or optionally any two of $R^2$, $R^3$, $R^4$ and $R^5$ are joined together to fonn a three- to seven-membered ring, having from 0 to 3 heteroatoms as ring members, or $R^2$ and $R^4$ taken together form a second bond between the carbon atoms to which each is attached, or $R^2$, $R^3$, $R^4$ and $R^5$ taken together represent a second and third bond between the carbon atoms to which each is attached;

$R^6$, $R^7$, $R^8$ and $R^9$ are each members independently selected from the group consisting of hydrogen, fluorine and substituted or unsubstituted ($C_1$–$C_8$)alkyl, or optionally any two of $R^6$, $R^7$, $R^8$ and $R^9$ are joined together to form a three- to seven-membered ring, having from 0 to 3 heteroatoms as ring members;

$R^1$ is a member selected from the group consisting of substituted or unsubstituted ($C_3$–$C_8$)cycloalkyl, substituted or unsubstituted ($C_3$–$C_8$)heterocycloalkyl, substituted or unsubstituted aryl and substituted or unsubstituted heteroaryl;

X is a member selected from the group consisting of O, S and N—$R^{11}$,
wherein $R^{11}$ is a member selected from the group consisting of H, ($C_1$–$C_8$)alkyl, substituted ($C_1$–$C_8$) alkyl, aryl, substituted aryl, heteroaryl, substituted heteroaryl, aryl($C_1$–$C_4$)alkyl, substituted aryl ($C_1$–$C_4$)alkyl, —CN, —C(O)$R^{12}$, —O$R^{13}$, —N$R^{13}R^{14}$, —C(O)N$R^{13}R^{14}$, and —S(O)$_2$N$R^{13}R^{14}$;
wherein $R^{12}$ is a member selected from the group consisting of ($C_1$–$C_8$)alkyl, substituted ($C_1$–$C_8$) alkyl, aryl, substituted aryl, heteroaryl, substituted heteroaryl, aryl($C_1$–$C_4$)alkyl and substituted aryl ($C_1$–$C_4$)alkyl; and
$R^{13}$ and $R^{14}$ are each members independently selected from the group consisting of hydrogen, ($C_1$–$C_8$)alkyl, substituted ($C_1$–$C_8$)alkyl, aryl, substituted aryl, heteroaryl, substituted heteroaryl, aryl($C_1$–$C_4$)alkyl and substituted aryl($C_1$–$C_4$)alkyl, or $R^{13}$ and $R^{14}$ can be combined with the nitrogen to which each is attached to form a 5-, 6- or 7-membered ring optionally having additional heteroatoms at the ring vertices; and m, n, p and q are each independently an integer of from 0 to 1, with the proviso that at least one of m, n, p or q is 1.

In one embodiment, X of the compound is O. In another embodiment, m and n of the compound are zero. In another embodiment, m of the compound is 1 and n of the compound is zero. In another embodiment, m and n of the compound are each 1. In another embodiment, m and n of the compound are each 1. In another embodiment, m and p of the compound are each zero, and n and q of the compound are each 1. In another embodiment, m, n, p and q of the compound are each 1. In another embodiment, $R^2$ and $R^4$ of the compound, taken together, form a second bond joining the carbon atoms to which each is attached, wherein m and p of the compound are each 1, $R^2$, $R^3$, $R^6$ and $R^7$ of the compound are each hydrogen, n and q of the compound are each zero, and $R^{10}$ of the compound is selected from the group consisting of substituted or unsubstituted aryl and substituted or unsubstituted heteroaryl, e.g., $R^{10}$ of the compound is substituted aryl having from one to three substituents selected from the group consisting of halogen, halo($C_1$–$C_4$)alkyl, halo($C_1$–$C_4$)alkoxy, ($C_1$–$C_4$)alkyl, ($C_1$–$C_4$)alkoxy, nitro, cyano, phenyl and methylenedioxy. In another embodiment, m, n, p and q of the compound are each 1, and $R^2$, $R^3$, $R^4$, $R^5$, $R^6$, $R^7$, $R^8$ and $R^9$ of the compound are each hydrogen. In another embodiment, m, n, p and q of the compound are each 1; $R^2$, $R^3$, $R^4$, $R^5$, $R^6$, $R^7$, $R^8$ and $R^9$ of the compound are each hydrogen; and $R^{10}$ of the compound is selected from the group consisting of substituted or unsubstituted aryl and substituted or unsubstituted heteroaryl. In another embodiment, $R^1$ of the compound is selected from the group consisting of substituted or unsubstituted branched ($C_3$–$C_8$)alkyl, and substituted or unsubstituted ($C_3$–$C_8$)cycloalkyl.

DETAILED DESCRIPTION OF THE INVENTION

Introduction

Figure 1:
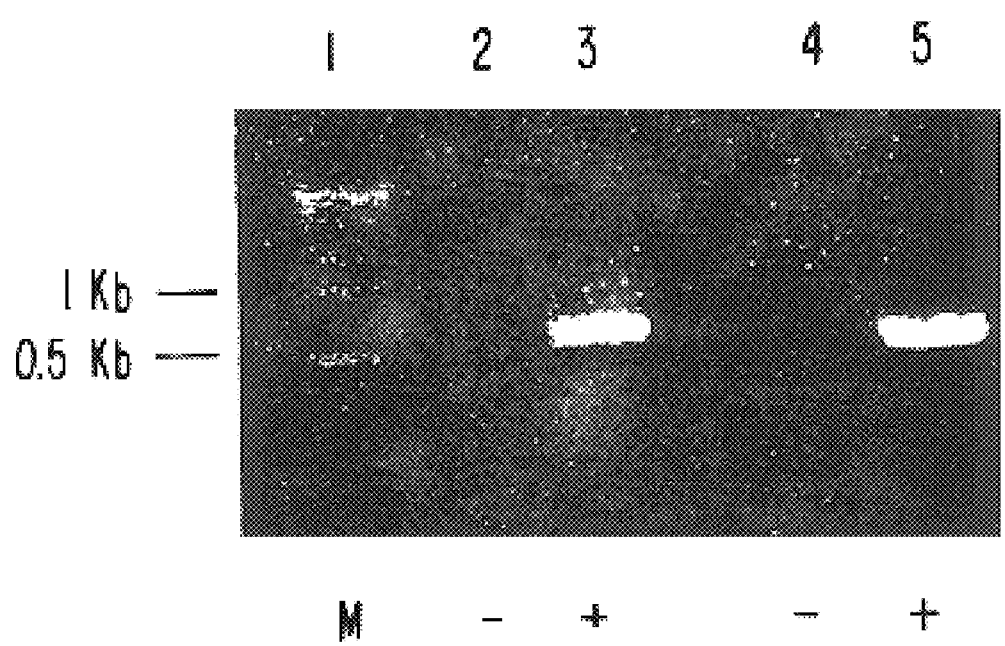
FIG. 1 shows expression of KCNQ2 and KCNQ3 mRNA in human dorsal root ganglion cells.

Ion channels of the KCNQ family have only recently been cloned and expressed. These voltage-gated potassium channels underlie the M-current, which functions to control resting membrane potential and excitability in a variety of neuronal cells (see, e.g., Wang et al., Science 282:1890–1893 (1998)). This application shows that KCNQ channels and M-currents are expressed in neurons of the dorsal root ganglion, which are an important part of the sensory neuronal pathway involved in pain.

The development of therapeutic agents, which act on potassium ion channels, has received considerable recent attention. One group has described a family of N-alkyl benzamides that act by blocking IKs potassium channels (see PCT/US98/02364, published as WO 98/37068). Bioactive compounds based on a benzanilide motif are known for the treatment of other disorders such as circulatory disturbances (Arita et al., U.S. Pat. No. 5,958,944), fungal infections (Baker et al., U.S. Pat. No. 4,845,107), inflammation (Beeley et al., U.S. Pat. No. 5,340,827) and ulcers and bacterial infections (Nishino et al., U.S. Pat. No. 5,859,032). The previous benzanilides do not include the 2-substituted-5-aminopyridine substructure found in certain compounds of the present invention. Moreover, none of the known benzanilide analogues are disclosed to open potassium channels or to be of use in treating conditions involving the modulation of potassium channels. Surprisingly, however, the N-aryl benzamides and related compounds provided herein, act to reduce pain and anxiety by opening the KCNQ potassium channels.

A. Treatment of Pain with KCNQ Channel Openers

This application demonstrates for the first time that openers of KCNQ channels (e.g., KCNQ2/3 heteromeric channels) alleviate pain, as assessed by two in vivo experimental procedures routinely used by the pharmaceutical industry to identify analgesic drugs. The mechanism for treating pain by opening KCNQ channels was previously unknown. However, the present application provides a mechanism for treating pain disorders, and an assay for identifying compounds that open KCNQ potassium channels and reduce pain. Modulation of KCNQ-type channels therefore represents a novel approach to the treatment of pain, including both somatic and neuropathic pain. In particular, modulation of KCNQ channels is used for pain syndromes not treatable by opiates or non-steroidal anti-inflammatory drugs. Such drugs that open KCNQ channels should also be free of the side-effects associated with opiates (e.g., addiction and respiratory depression) or non-steroidal anti-inflammatory drugs (gastrointestinal ulceration).

In the present application, cultured DRGs express a non-inactivating, slowly deactivating outward current similar to the M-current. DRGs are an important component of the sensory pathways responsible for pain perception. Furthermore, compounds have been synthesized that selectively increase the flow of potassium ions through a cloned human KCNQ2/3 heteromeric ion channel expressed in CHO cells (see FIG. 1) as well as endogenous KCNQ2/3 channels expressed in DRGs (see FIG. 2). In CHO cells, such a compound increased outward current at a holding potential of −30 mV and induced a 5 to 10 mV hyperpolarization of the resting membrane potential.

Figure 3:
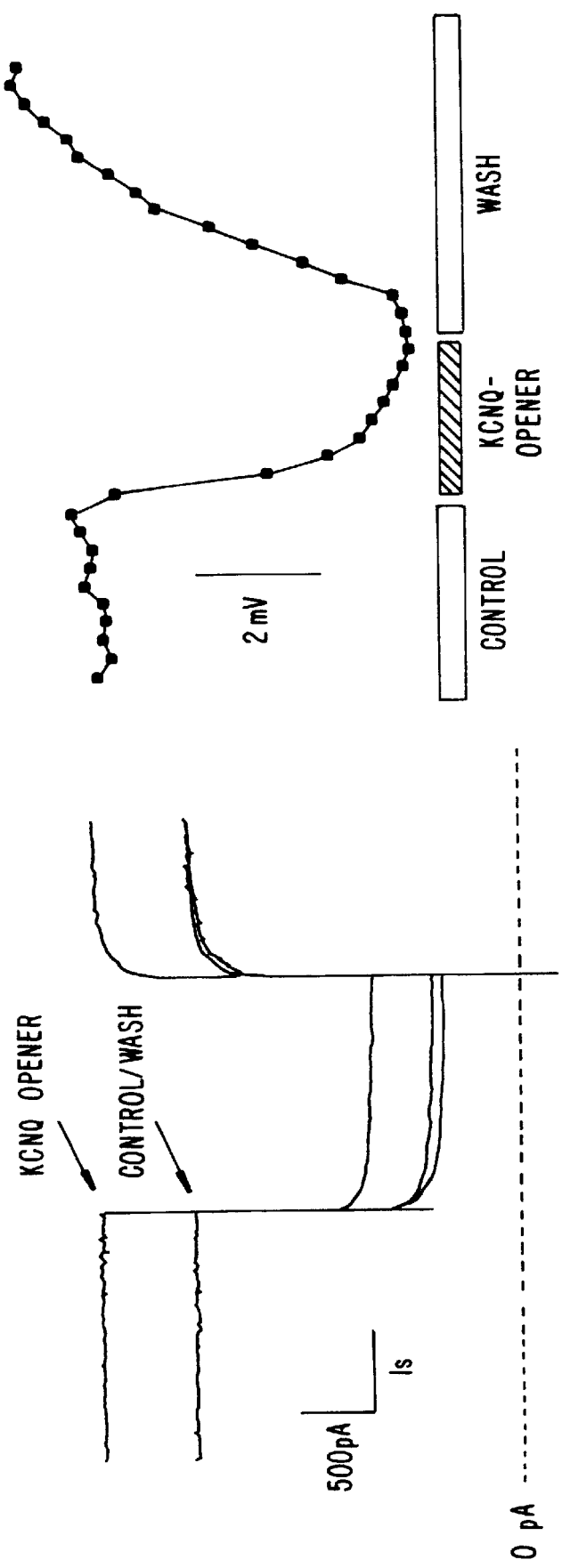
FIG. 3 shows that a KCNQ channel opener increases holding current at −30 mV (left panel) and hyperpolarizes the membrane potential (right panel) in cultured rat dorsal root ganglion cells.

The analgesic effect of a KCNQ2/3 opener was assessed in vivo, using the formalin algesia test and the hotplate test. In the formalin algesia test, mice were administered a dose of a KCNQ opener. Thirty minutes later, a formalin solution was injected into a paw. For thirty minutes immediately following the injection, mice were observed and the time spent licking the paw (a response to pain) was measured (see FIG. 3). Untreated mice spent substantially more time licking paw than untreated mice. In the hotplate test, mice were administered a dose of the KCNQ opener. One hour later the mouse was place on a heated metal surface. When the mouse licked its paw, it was removed from the surface, and time to lick the paw was measured. Both tests showed statistically significant differences between treated and untreated mice.

These assays demonstrate that administration of a KCNQ modulator, i.e., a selective KCNQ2/3 channel opener, reduces pain in a subject animal. Thus, KCNQ channel openers can be used to treat pain. Such modulators are identified using the in vitro and in vivo assays described herein.

B. Treatment of Anxiety with KCNQ Channel Openers

Moreover, this application demonstrates for the first time that openers of KCNQ channels (e.g., KCNQ2/3 heteromeric channels) alleviate anxiety, as assessed by an in vivo experimental procedure routinely used by the pharmaceutical industry to screen for drugs effective for the treatment of generalized anxiety disorder. The mechanism for treating anxiety by opening KCNQ potassium channels was previously unknown. However, the present application provides a mechanism for treating anxiety disorders, and an assay for identifying compounds that open KCNQ potassium channels and reduce anxiety. Modulation of KCNQ channels therefore represents a novel approach to treatment of anxiety disorders such as generalized anxiety disorder, panic disorder, and stress disorder, e.g., acute or post-traumatic. Such drugs that open KCNQ channels should also be free of the abuse liability and tolerance associated with benzodiazepines (e.g., VALIUM®, LIBRIUM®).

Figure 6:
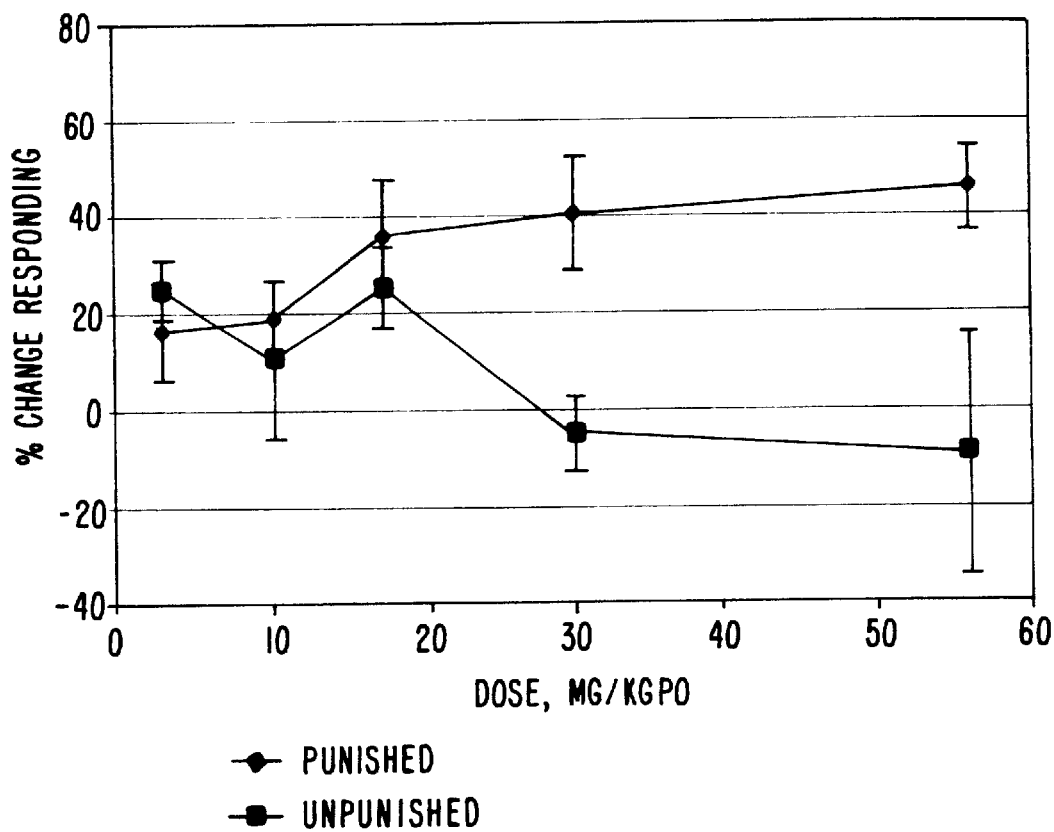
FIG. 6 shows that a KCNQ channel opener increases responding in the punished phase of Geller conflict procedure in rat in a dose dependent manner. Increases in punished responding were statistically significant, $p<0.05$, paired t-test, at 10, 17, and 56 mg/kg. Responding during the unpunished phase is not disrupted.
Figure 7:
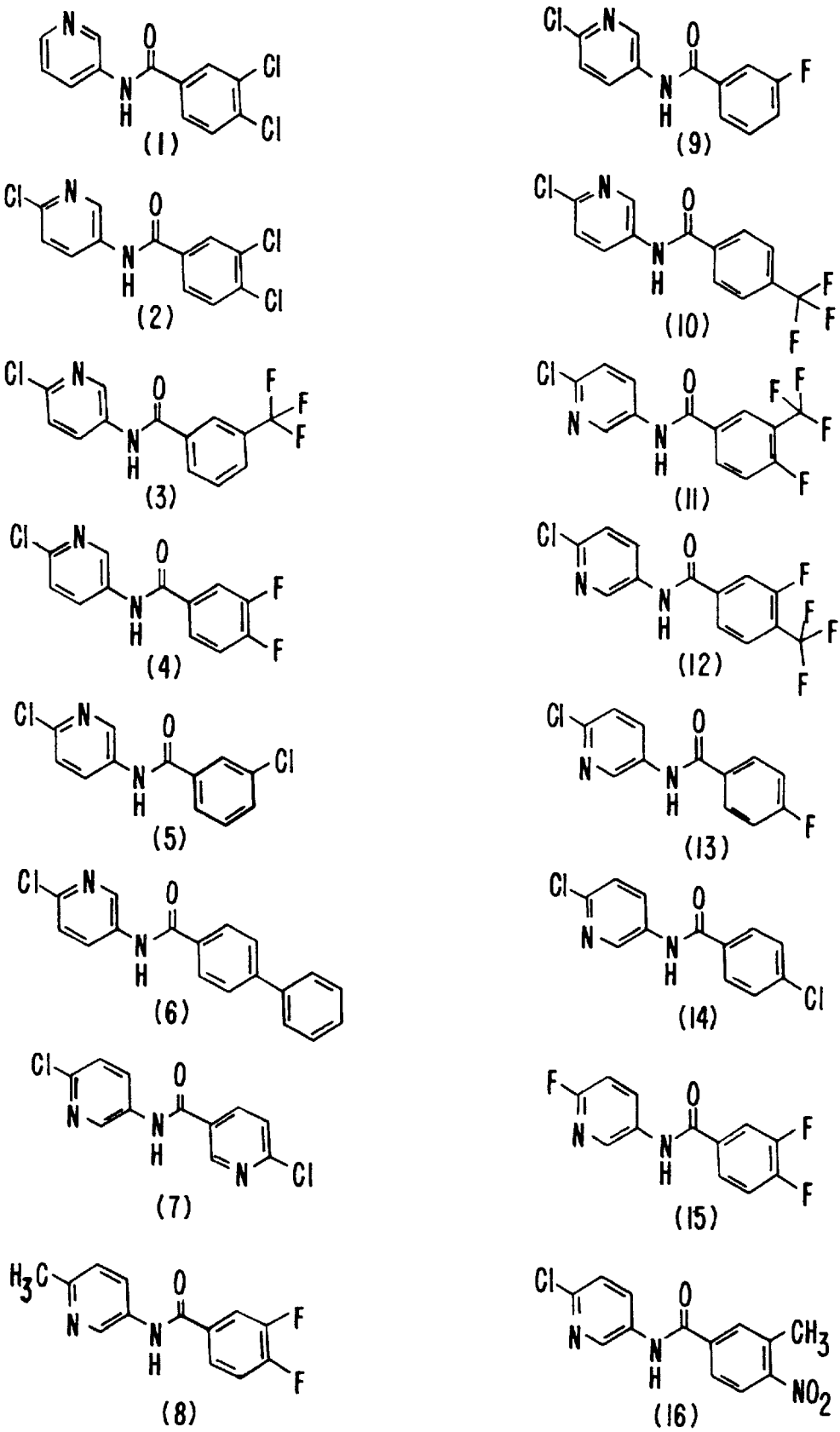
FIG. 7 shows some compounds of the invention.
Figure 7:
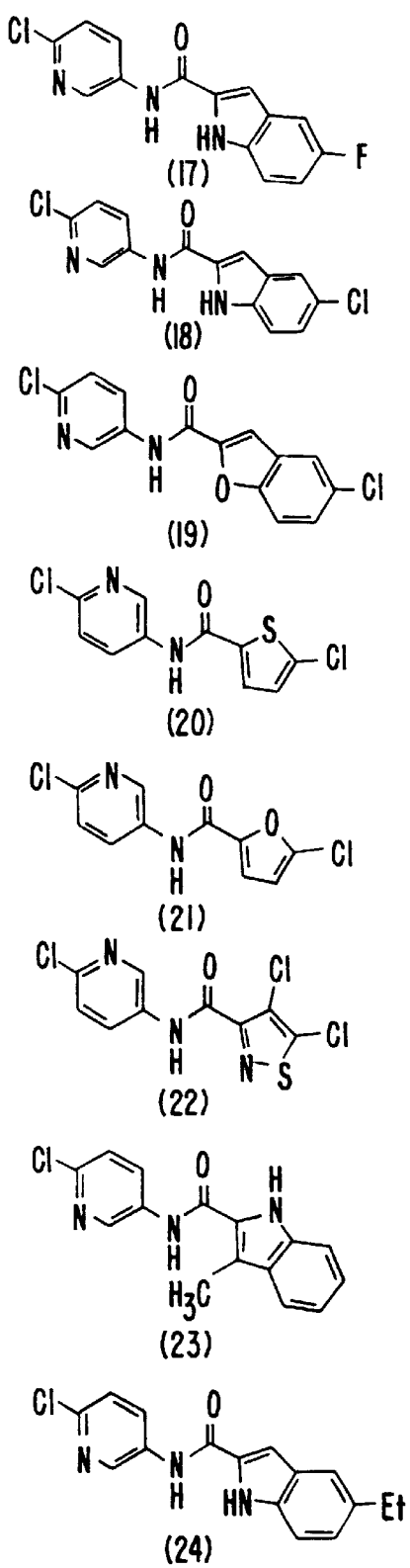
Figure 7:
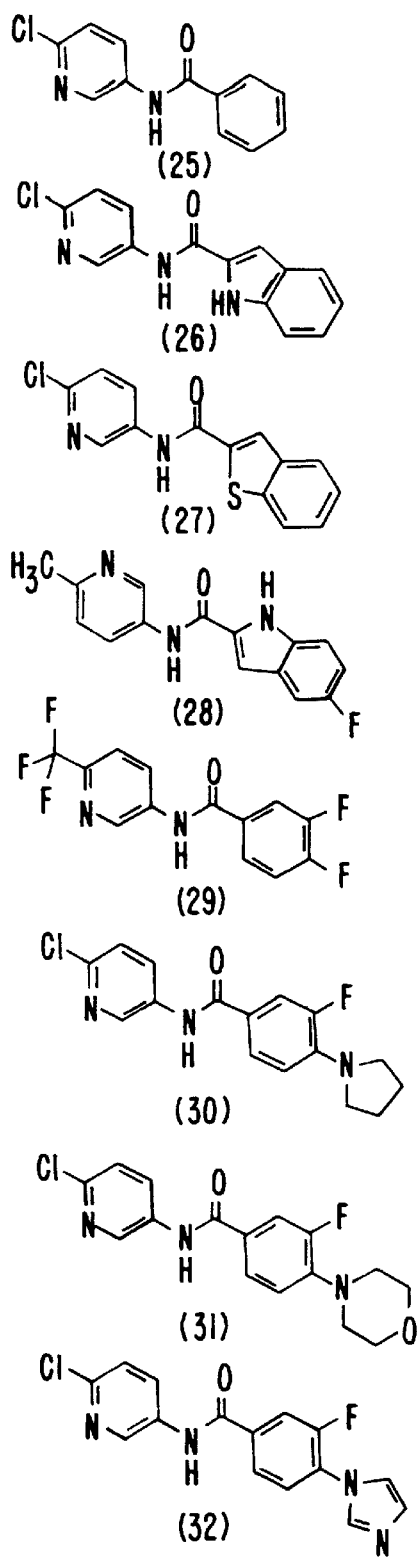
Figure 7:
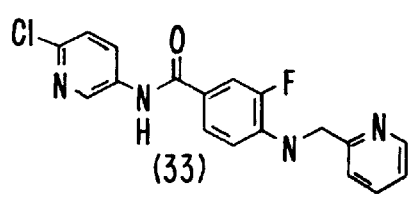
Figure 7:
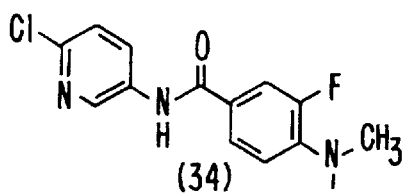
Figure 7:
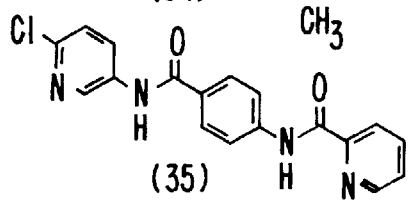
Figure 7:
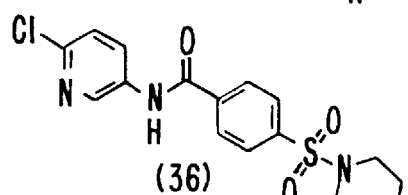
Figure 7:
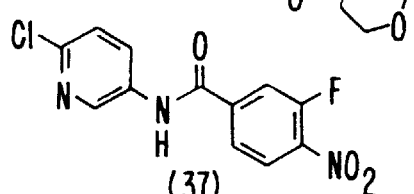
Figure 7:
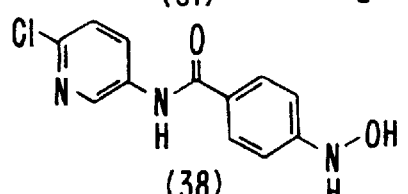
Figure 7:
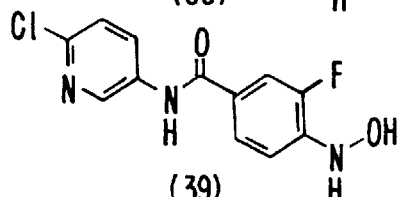
Figure 7:
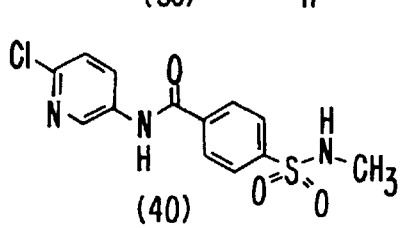
Figure 7:
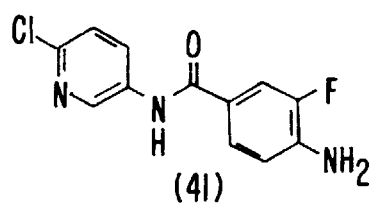
Figure 7:
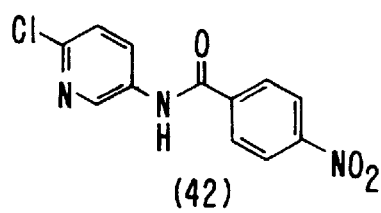
Figure 7:
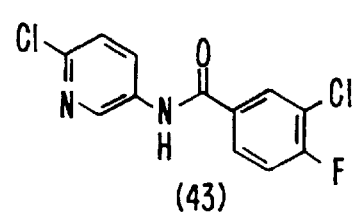
Figure 7:
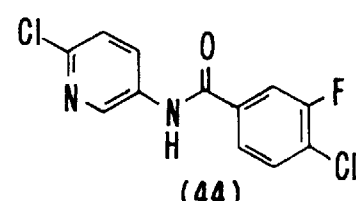
Figure 7:
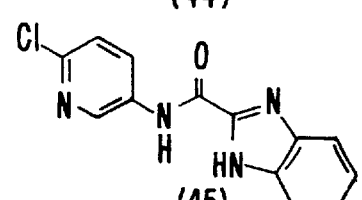
Figure 7:
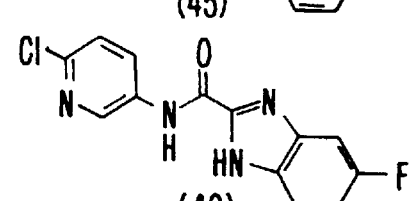
Figure 7:
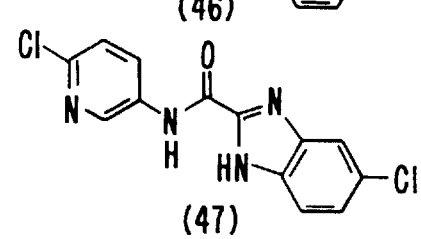
Figure 7:
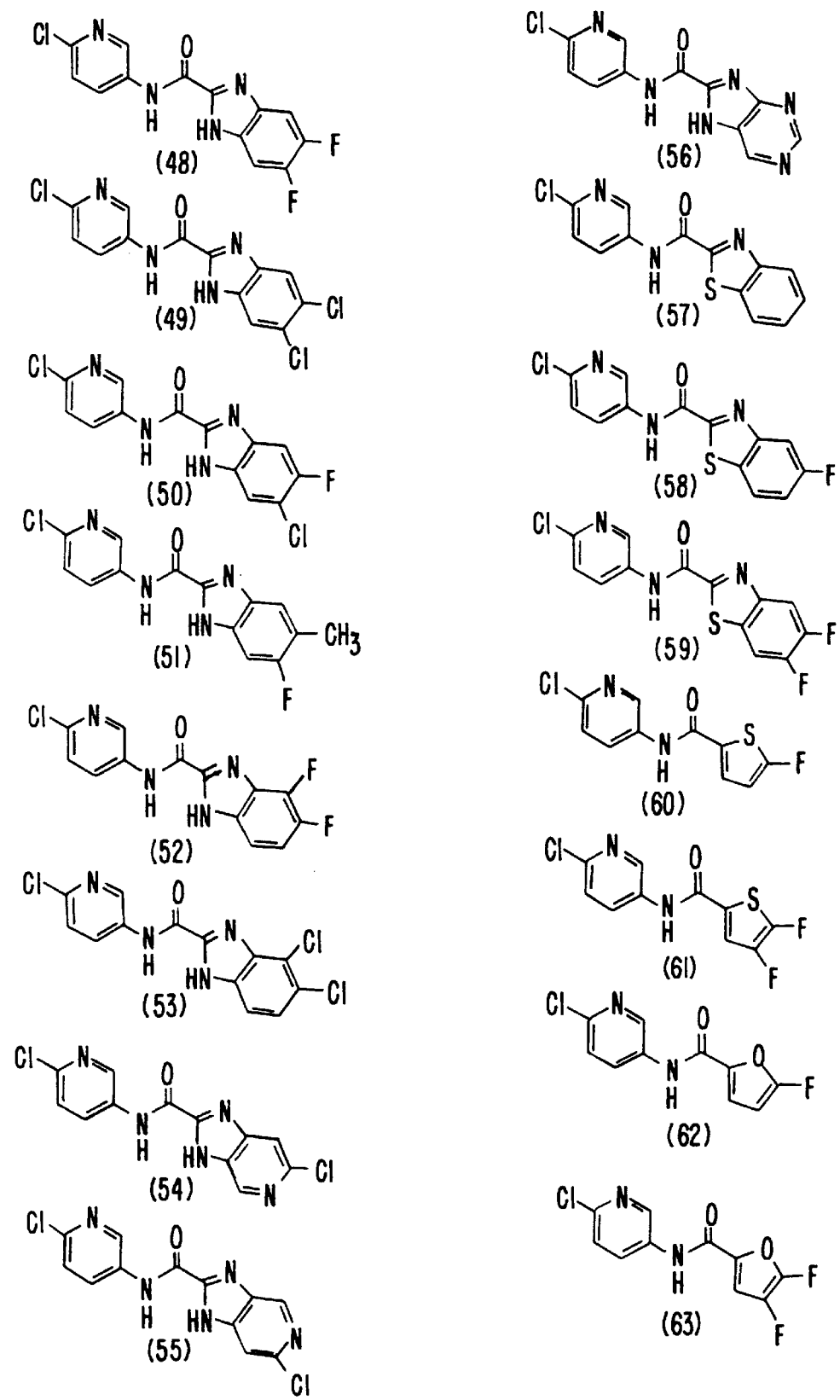
Figure 7:
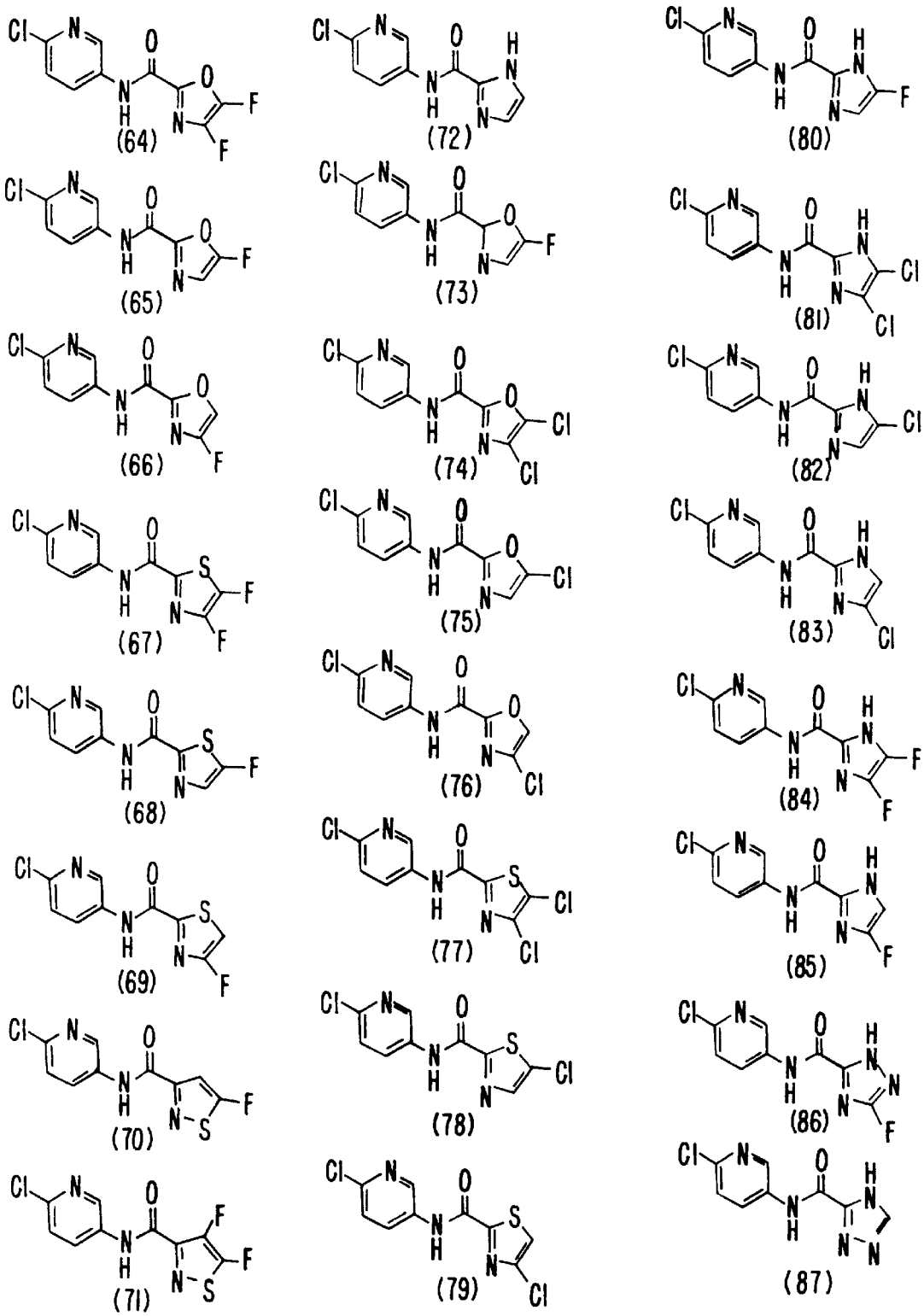
Figure 7:
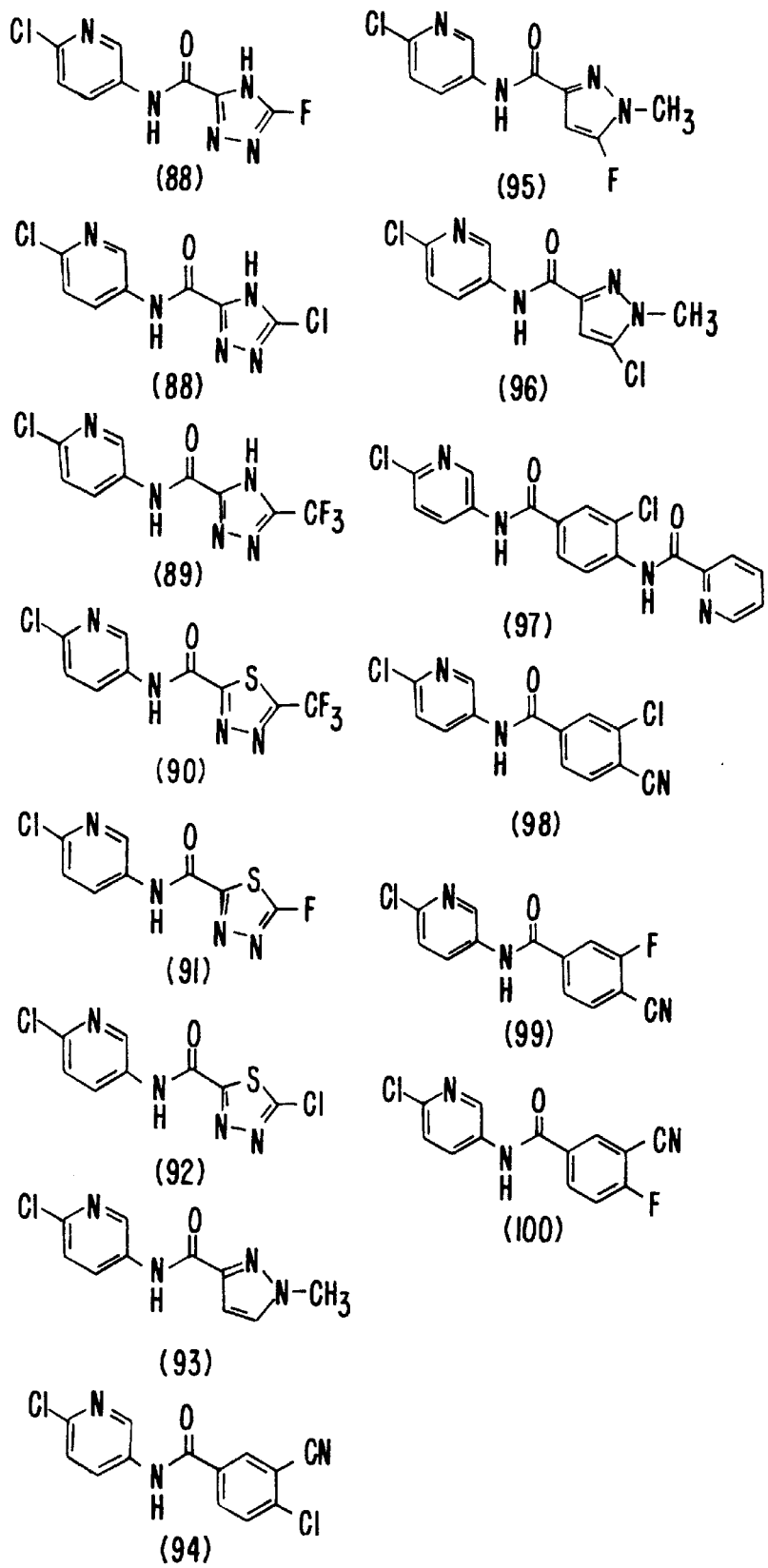

All rapid-onset anxiolytics on the market (c.g., benzodiazepines, barbiturates, and propanediol carbamates) increase behavior that has been suppressed by punishment. Non-anxiolytics generally do not increase punished behavior, or do so to a much lesser extent (Howard & Pollard, *Pharm. & Ther.* 45:403–424 (1990); Howard & Pollard, *Psycopharmacology of Anxiolytics and Antidepressants,* pp. 131–153 (1991)). The standard test in rat to measure anxiolytic effect (Geller conflict procedure) was designed by Geller and Seifter and modified by Pollard and Howard (Geller & Seifter, *Psychophamracologia* 1:482–492 (1960: Pollard & Howard, *Psychopharmacology* 62:117–121 (1979)). The anxiety-reducing effect of a KCNQ2/3 channel opener was measured using the Geller conflict procedure in rats. Rats are trained to press a lever to receive food pellets during daily 1 hour sessions. The sessions are divided into punished and unpunished phases. During the four, three-minute punished periods, a light signals that each lever press will produce both a pellet and a foot shock (punishment), which reduces lever pressing. The number of punished lever presses on test days (when test compound is administered) is compared to the mean on baseline days. The positive control, chlordiazepoxide, increases punished lever pressing by >50%. A compound that produces an increase of approximately 40% or greater is generally considered to be of interest as a rapid-onset anxiolytic. A selective KCNQ2/3 channel opener increased punished responding in a dose dependent, statistically significant manner (FIG. 6).

These assays demonstrate that administration of a KCNQ modulator, i.e., a selective KCNQ2/3 channel opener, reduces anxiety in a subject animal. Thus, KCNQ channel openers can be used to treat anxiety disorders. Such modulators are identified using the in vitro and in vivo assays described herein.

Definitions

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine,* pp. 93–98 (Wilson et al., eds., 12th ed. 1991); Williams et al., *J. of Medicinal Chem.* 42:1481–1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Anxiety" refers to psychiatric syndromes characterized by a subjective sense of unease, dread, or foreboding, e.g., panic disorder, generalized anxiety disorder, and stress disorders, e.g., acute and post-traumatic. Diagnostic criteria for these disorders are well known to those of skill in the art (see, e.g., *Harrison's Principles of Internal Medicine,* pp. 2486–2490 (Wilson el al., eds., 12th ed. 1991)

"KCNQ potassium channel" refers to heteromeric or homomeric potassium channels composed of at least one alpha subunit from the KCNQ polypeptide family, as described below.

"KCNQ polypeptide" or "KCNQ subunit" refers to a polypeptide that is a subunit or monomer of a voltage-gated, KCNQ potassium channel, a member of the KCNQ gene family, and a member of the Kv superfamily of potassium channel monomers. When a KCNQ polypeptide, e.g., KCNQ 1, 2, 3, or 4, is part of a KCNQ potassium channel, either a homomeric or heteromeric potassium channel, the channel has voltage-gated activity. The term KCNQ polypeptide therefore refers to polymorphic variants, alleles, mutants, and interspecies homologs that: (1) have a sequence that has greater than about 60% amino acid sequence identity, preferably about 65, 70, 75, 80, 85, 90, or 95% amino acid sequence identity, to a KCNQ gene family member such as those described in Biervert et al., *Science* 279:403–406, Kubisch et al., *Cell* 96:437–446 (1999), Yang et al., *J. Biol. Chem.* 273:19419–19423 (1998); Wang et al., *Nature Genet.* 12:17 (1996); Wei et al., *Neuropharmacol.* 35:805 (1996); Singh et al., *Nature Genet.* 18:25 (1998); Charlier et al., *Nature Genet.* 18:53 (1998); WO99/31232; and WO99/07832 (herein each incorporated by reference in their entirety); (2) bind to antibodies, e.g., polyclonal antibodies, raised against an immunogen comprising a KCNQ gene family member polypeptide, as described above, and conservatively modified variants thereof; (3) specifically hybridize under stringent hybridization conditions to a sequence encoding a KCNQ gene family member polypeptide, as described above, and conservatively modified variants thereof; or (4) are amplified by primers that specifically hybridize under stringent hybridization conditions a sequence encoding a KCNQ gene family polypeptide, as described above.

KCNQ potassium channels, KCNQ polynucleotides, and KCNQ nucleic acids are identified, isolated, expressed, purified, and expressed in recombinant cells according to methods well known to those of skill in the art.

Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1 % SDS at 65° C.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 85%, 90%, or 95% identity), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

Algorithms suitable for determining percent sequence identity are the BLAST and BLAST 2.0 algorithms, which are described in Altschul et al, *Nuc. Acids Res.* 25:3389–3402 (1977) and Altschul et al., *J. Mol. Biol.* 215:403–410 (1990), respectively. The BLASTN program (for nucteotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Inhibitors," "activators" "openers," or "modulators" of voltage-gated potassium channels comprising a KCNQ subunit refer to inhibitory or activating molecules identified using in vitro and in vivo assays for KCNQ channel function. In particular, inhibitors, activators, and modulators refer to compounds that increase KCNQ channel function, thereby reducing pain in a subject, as assayed using a formalin algesia test or a hotplate test in vivo, or thereby reducing anxiety in a subject, as assayed using a Geller conflict test (see Example section). Inhibitors are compounds that decrease, block, prevent, delay activation, inactivate, desensitize, or down regulate the channel, or speed or enhance deactivation. Activators are compounds that increase, open, activate, facilitate, enhance activation, sensitize or up regulate channel activity, or delay or slow inactivation. Such assays for inhibitors and activators also include, e.g., expressing recombinant KCNQ in cells or cell membranes (e.g., CHO cells expressing recombinant KCNQ channels, see Example section) and then measuring flux of ions through the channel directly or indirectly. Alternatively, cells expressing endogenous KCNQ channels can be used in such assays (e.g., rat dorsal root ganglion cells expressing endogenous KCNQ channels, see Example section).

To examine the extent of inhibition, samples or assays comprising a KCNQ channel are treated with a potential activator or inhibitor compound and are compared to control samples without the test compound. Control samples (untreated with test compounds) are assigned a relative KCNQ activity value of 100%. Inhibition of channels comprising a KCNQ subunit is achieved when the KCNQ activity value relative to the control is about 90%, preferably 50%, more preferably 25–0%. Activation of channels comprising a KCNQ subunit is achieved when the KCNQ activity value relative to the control is 110%, more preferably 150%, most preferably at least 200–500% higher or 1000% or higher.

An amount of compound that activates or inhibits a KCNQ channel, as described above, is a "potassium channel modulating amount" of the compound, which thereby reduces pain in a subject.

The phrase "modulating ion flow," or "increasing ion flow" in the context of assays for compounds affecting ion flux through a KCNQ channel, for the purposes of reducing pain in a subject, includes the determination of any parameter that is indirectly or directly under the influence of the channel. It includes physical, functional and chemical effects, e.g., changes in ion flux including radioisotopes, current amplitude, membrane potential, current flow, transcription, protein binding, phosphorylation, dephosphorylation, second messenger concentrations (cAMP, cGMP, $Ca^{2+}$, $IP_3$), ligand binding, and other physiological effects such as hormone and neurotransmitter release, reduction in pain, as well as changes in voltage and current. The ion flux can be any ion that passes through a channel and analogues thereof, e.g., potassium, rubidium, sodium. Such functional, chemical or physical effects can be measured by any means known to those skilled in the art, e.g., patch clamping, voltage-sensitive dyes, whole cell currents, radioisotope efflux, inducible markers, in vivo pain assays such as formalin algesia or the hotplate test, and the like.

"Biologically active" KCNQ refers to a KCNQ subunit that has the ability to form a potassium channel having the characteristic of voltage-gating tested as described above.

"Homomeric channel" refers to a KCNQ channel composed of identical alpha subunits, whereas "heteromeric channel" refers to a KCNQ channel composed of at least two different types of alpha subunit from a related gene family, e.g., KCNQ2 and KCNQ3. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "voltage-gated" activity or "voltage-gating" or "voltage dependence" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium at membrane potentials more positive than the reversal potential for potassium ($E_K$) in typical cells, because they have greater probability of being open at such voltages. $E_K$ is the membrane potential at which there is no net flow of potassium ions because the electrical potential (i.e., voltage potential) driving potassium efflux is balanced by the concentration gradient for potassium. The membrane potential of cells depends primarily on their potassium channels and is typically between −60 and −100 mV for mammalian cells. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Nonner, in *Potassium Channels*, pp. 40–60 (Cook, ed., 1990)). The characteristic of voltage gating can be measured by a variety of techniques for measuring changes in current flow and ion flux through a channel, e.g., by changing the $[K^+]$ of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

For the KCNQ modulating compounds of the invention, the term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl." Alkyl groups which are limited to hydrocarbon groups are termed "homoalkyl".

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, -SiR'R"R'", —OC(O)R', —C(O)R', —CO$_2$R', —CONR'R", —OC(O)NR'R", —NR"C(O)R', —NR'—C(O)NR'R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', ,—NR'—C(O)NR"R'", —NH—C(NH$_2$)

=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$–C$_4$)alkoxy, and perfluoro(C$_1$–C$_4$)alkyl, in a number ranging from zero to the total number of open valences on the aromatic ring system; and where R', R" and R'" are independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl) oxy-(C$_1$–C$_4$)alkyl.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al., *Journal of Pharmaceutical Science* 66:1–19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Assays for Modulators of KCNQ Potassium Channels

A. Assays

The activity of a potassium channel comprising a KCNQ polypeptide, in particular a channel comprising KCNQ 2 and/or KCNQ3, can be assessed using a variety of in vitro and in vivo assays. Preferably, the in vivo assays disclosed herein in the example section are used to identify KCNQ openers for treatment of pain or anxiety. Such assays are used to test for inhibitors and activators of KCNQ channels, for the identification of compounds that reduce pain or anxiety in a subject. Assays for modulatory compounds include, e.g., measuring current; measuring membrane potential; measuring ion flux; e.g., potassium or rubidium; measuring potassium concentration; measuring second messengers and transcription levels, using potassium-dependent yeast growth assays; measuring pain responses in mice, e.g., with formalin algesia or hotplate assays; measuring ligand binding; and using, e.g., voltage-sensitive dyes, radioactive tracers, and patch-clamp electrophysiology.

Modulators of the potassium channels are tested using biologically active KCNQ channels, either recombinant or naturally occurring. KCNQ channels, preferably human KCNQ channels, can be isolated in vitro, co-expressed or expressed in a cell, or expressed in a membrane derived from a cell. In such assays, a KCNQ polypeptide is expressed alone to form a homomeric potassium channel or is co-expressed with a second alpha subunit (e.g., another KCNQ family member) so as to form a heteromeric potassium channel (e.g., KCNQ2/3). A KCNQ channel can also be expressed with additional beta subunits. Modulation by a compound is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of KCNQ channels is achieved when the potassium channel activity value relative to the control is about 90%, preferably 50%, more preferably 25–0%. Activation of KCNQ channels is achieved when the potassium channel activity value relative to the control is 110%, more preferably 150%, more preferably 200–500% higher, preferably 1000% or higher. Compounds that increase the flux of ions will cause a detectable increase in the ion current density by increasing the probability of a KCNQ channel being open, by decreasing the probability of it being closed, by increasing conductance through the channel, and/or by allowing the passage of ions.

Changes in ion flux may be assessed by determining changes in polarization (i.e., electrical potential) of the cell or membrane expressing the KCNQ potassium channel. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM. Cells expressing the channel can express recombinant KCNQ (e.g., CHO cells or Xenopus cells) or endogenous KCNQ channels (e.g., rat dorsal root ganglion).

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $Ca^{2+}$, or cyclic nucleotides. KCNQ orthologs will generally confer substantially similar properties on a channel comprising a KCNQ polypeptide, as described above. Preferably human KCNQ channels are used in the assays of the invention. Optionally, KCNQ orthologs from other species such as rat or mouse, preferably a mammalian species, are used in the assays of the invention.

B. Modulators

The chemical compounds of the invention, which increase ion flux through KCNQ potassium channels, are made according to methodology well known to those of skill in the art. For example, synthesis of benzanilides is described in U.S. Ser. No. 60/147,221, filed Aug. 4, 1999, and synthesis of secondary amides is described in U.S. Ser. No. 60/158,712, filed Oct. 8, 1999.

The compounds tested as modulators of KCNQ channels can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a KCNQ channel is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention.

Preparation of Potassium Channel Openers

Compounds of the present invention can be prepared using readily available starting materials or known intermediates. Briefly, the synthesis of N-aryl benzamides herein or secondary amides herein involves formation of a single amide bond from a "carbonyl component" (typically a carboxylic acid, carboxylic acid chloride, ester or an activated form of a carboxylic acid, for example, a symmetrical or mixed anhydride) and an "amine component" (typically, an aniline, aniline derivative, amino heterocycle, and the like). General and specific procedures for the preparation of the present compounds are provided in the examples below.

Other N-aryl benzamide compounds of the present invention can be prepared using standard procedures as outlined in Scheme 1a below. In this scheme, an N-phenyl benzamide (i, wherein $Y^1$ and $Y^2$ represent substituents, including multiple substituents on the aryl groups) can be treated with reagents such as Lawessons's reagent to provide the thioamides, ii. Alkylation of ii, with, for example, methyl iodide produces iii which can be converted to target structures iv, v and vi. Thus, treatment of iii with sodium hydride (or another suitable base) and sulfamide provides the sulfamoylimino derivative, iv. Similarly, treatment of iii with sodium hydride or another base, followed by cyanamide provides v. Conversion of v to vi can be accomplished with HCl.

One of skill in the art will recognize that other compounds of the present invention can be prepared from intermediates such as iii. For example, treatment of iii with a primary or secondary amine will provide amidine derivatives that are useful as described or they can be further derivatized.

SCHEME 1a

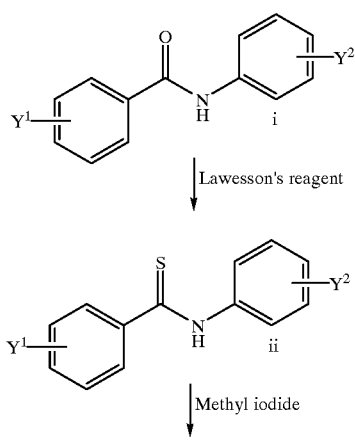

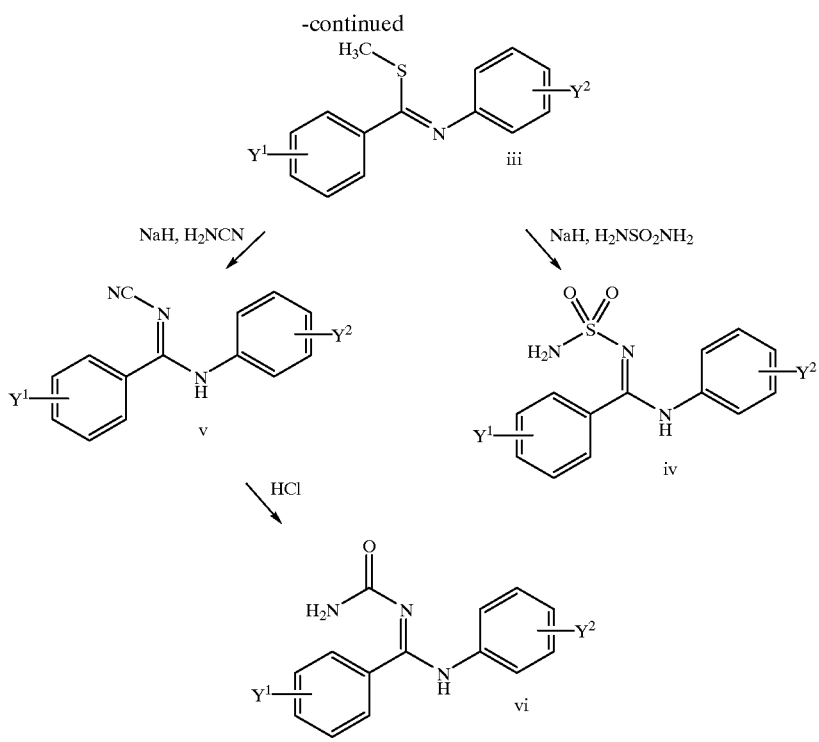

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a hetereofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

Other secondary amide compounds of the present invention can be prepared using standard procedures as outlined in Scheme 1b below. In this scheme, an amide (i, wherein R' and R" represent the groups $R^1$—$(C(R^2)(R^3))_m$—$(C(R^4)(R^5))_n$— and —$(C(R^6)(R^7))_p$—$(C(R^8)(R^9))_q$—$R^{10}$, respectively) can be treated with reagents such as Lawesson's reagent to provide the thioamides, ii. Alkylation of ii, with, for example, methyl iodide produces iii which can be converted to target structures iv, v and vi. Thus, treatment of iii with sodium hydride (or another suitable base) and sulfamide provides the sulfamoylimino derivative, iv. Similarly, treatment of iii with sodium hydride or another base, followed by cyanamide provides v. Conversion of v to vi can be accomplished with HCl.

One of skill in the art will recognize that other compounds of the present invention can be prepared from intermediates such as iii. For example, treatment of iii with a primary or secondary amine will provide amidine derivatives that are useful as described or can be further derivatized.

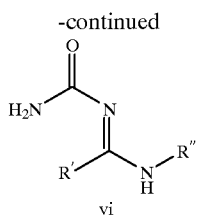

Administration and Pharmaceutical Compositions

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of pain, the compounds utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Expression of KCNQ2 and KCNQ3 mRNA in Human Dorsal Root Ganglion

Expression of KCNQ2 and KCNQ3 mRNA was detected by PCR amplification of human dorsal root ganglion (DRG)

cDNA. cDNA was prepared by reverse transcription of total RNA from human DRG using standard procedures. A second mock reverse-transcription reaction was also performed, which was identical to the first, except for the omission of the reverse transcriptase. 35 cycles of amplification were performed on a single microliter of human DRG cDNA, using oligonucleotide primers designed to amplify either KCNQ2 or KCNQ3.

For KCNQ2, the oligonucleotides used for the amplification were: 5'-GGCTCGGTCCCCCACAGTCAG-3' (sense) and 5'-CTCCACGGCAGGTCCAAGTCTCA-3' (antisense).

For KCNQ3, the oligonucleotides were: 5'-GCCCACGGTCCTGCCTATCTT-3' (sense) and 5'-CATTGGTGTCCCCGCTGGTAA-3' (antisense).

Figure 2:
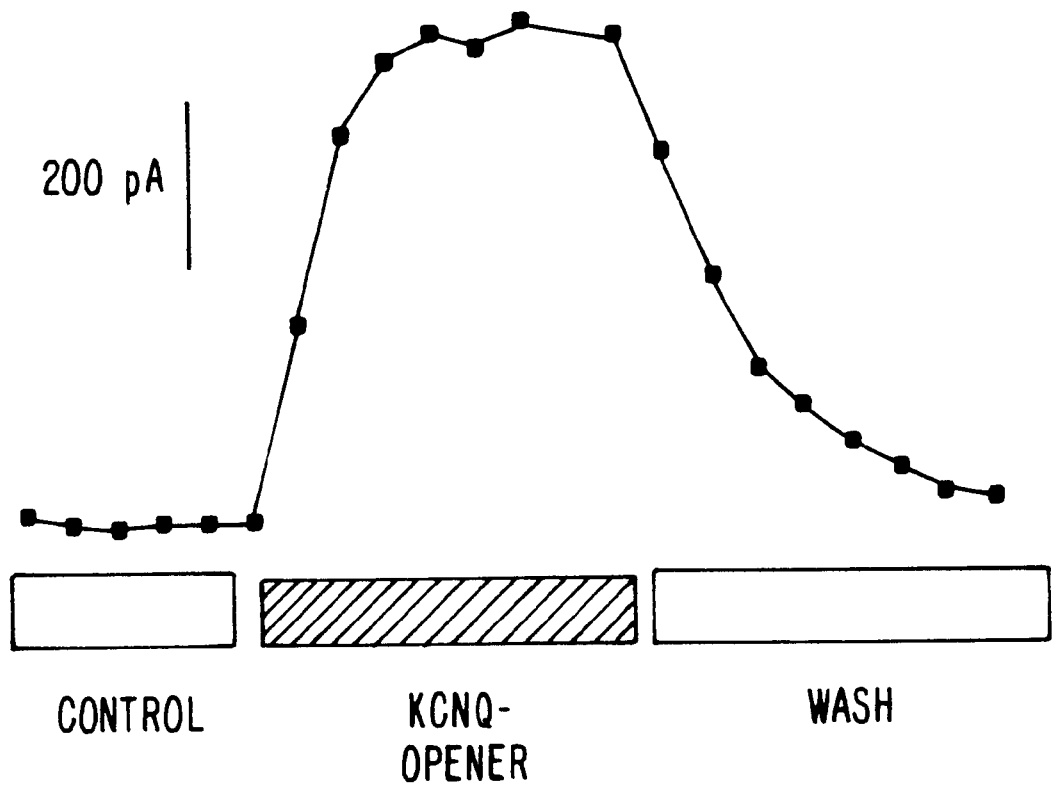
FIG. 2 shows a KCNQ channel opener compound that increases holding current at −40 mV in CHO cells stably expressing a KCNQ2/3 heteromeric potassium channel.

PCR amplified DNA fragments were separated by agarose gel electrophoresis, visualized using ethidium bromide staining and sized by comparison to DNA fragments of known size (see FIG. 1; M, lane 1). PCR failed to amplify KCNQ2 or KCNQ3 fragments from reverse-transcription samples generated in the absence of reverse transcriptase (−), indicating that the DRG RNA samples were not contaminated with genomic DNA. PCR did however, amplify both KCNQ2 (lane 3) and KCNQ3 (lane 5) from reverse transcribed cDNA samples, indicating that KCNQ2 and KCNQ3 mRNA are expressed in human dorsal root ganglion.

Example 2

Expression of Recombinant KCNQ2/3 Channel CHO Cells

A cloned KCNQ2/3 channel was expressed in chinese hamster ovary cells (CHO-K1 cells) according to standard methodology. CHO-K1 cells were transfected with human KCNQ2/3 nucleic acid using lipofectamine reagent according to the manufacturer's instructions. Cells stably expressing KCNQ2/3 were identified by their resistance to G418 (400 $\mu$g/ml). CHO-K1 cells stably transfected with the KCNQ2/3 tandem construct were maintained in Ham's F-12 supplemented with 10% heat-inactivated fetal bovine serum and 400 $\mu$g/ml G418 in an incubator at 37° C. with a humidified atmosphere of 5% $CO_2$.

For modulation of KCNQ channels, a benzanilide KCNQ channel opener was applied to the cells. The compound increased holding current at −40 mV (see FIG. 2) and hyperpolarized the membrane potential.

Example 3

Expression of Endogenous KCNQ2/3 Channel in DRGs

DRGs were isolated from 1 day old Sprague-Dawley rats. DRGs were dissociated using trypsin (0.25%) and protease type XXIII (2 mg/ml) and neurons were maintained in culture in 90% Eagles MEM (without L-glutamate), 10% FCS, 100 U/m; penicillin, 100 g/ml streptomycin, in an incubator at 37° C. with a humidified atmosphere of 5% $CO_2$.

As described above, a benzanilide KCNQ channel opener was applied to the cells. The opener increased holding current at −30 mV and hyperpolarized the membrane potential (see FIG. 3).

Example 4

In vivo Formalin Alaesia Test

The analgesic effect of a KCNQ modulator was assessed in vivo, using the formalin algesia test. All animal experiments were conducted in accordance with the Declaration of Helsinki and with the guide for the care and use of laboratory animals.

Figure 4:
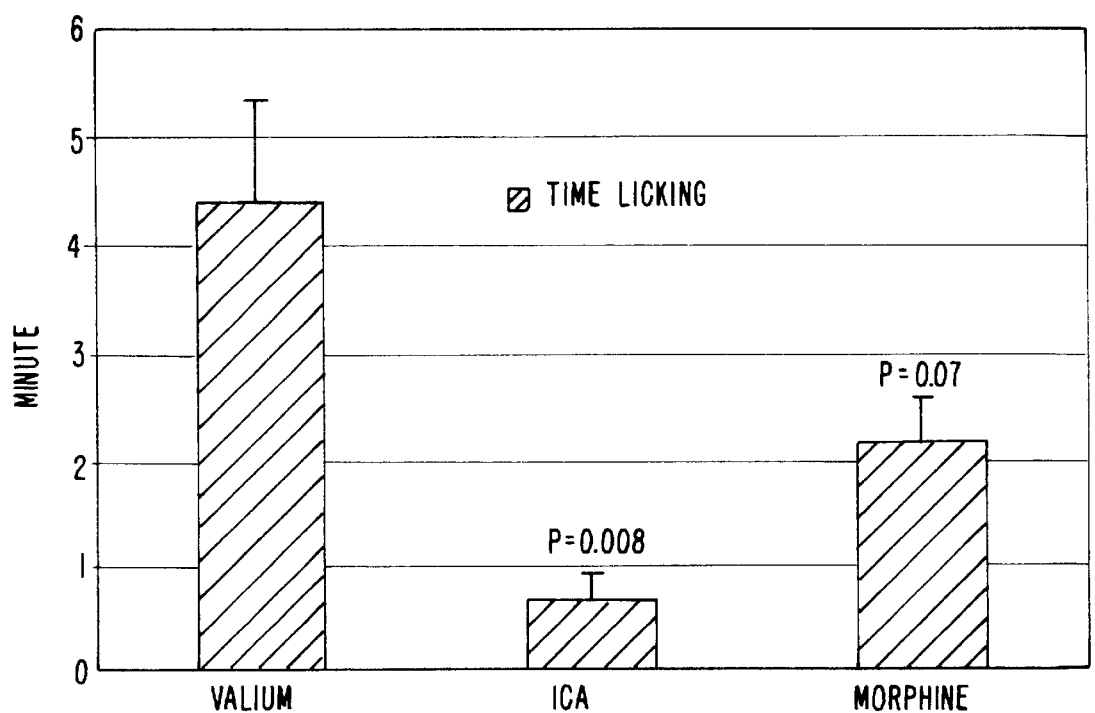
FIG. 4 shows that a KCNQ channel opener compound inhibits formalin algesia in mice. Test compounds were administered IP (KCNQ channel opener, 30 mg/kg) or PO (morphine, 3 mg/kg) 30 minutes prior to injection of 2.5% formalin into right hind paw of mice (n=4). P values were calculated by independent samples t-test.

In the formalin algesia test, mice were administered an IP dose of 30 mg/kg of a benzanilide KCNQ opener, or vehicle alone without opener as a control. Thirty minutes later, 20 $\mu$L of a 2.5% a formalin solution was injected into the plantar surface of the right hind paw. For thirty minutes immediately following the injection, mice were observed and the time spent licking the paw (a response to pain) was measured using a timer(see FIG. 4). Untreated mice spent more than four minutes licking the right hind paw, whereas mice treated with the KCNQ opener spent less than one minute licking the right hind paw (sig. p=0.0008).

Example 5

In vivo Hotplate Test for Pain

In the hotplate test, mice were administered an oral dose of 10, 30, or 100 mg/kg of a benzanilide KCNQ opener. All animal experiments were conducted in accordance with the Declaration of Helsinki and with the guide for the care and use of laboratory animals.

Figure 5:
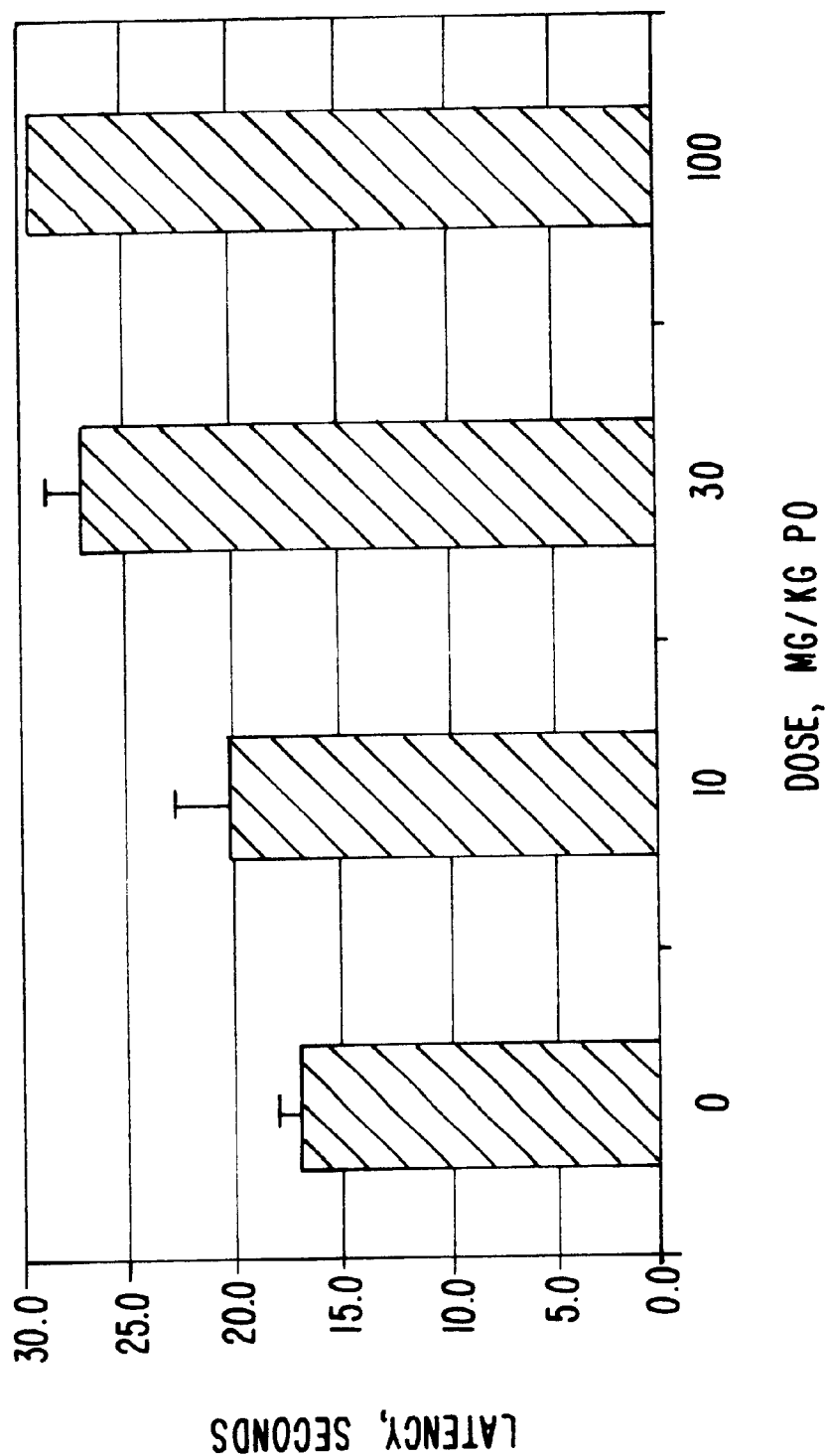
FIG. 5 shows that a KCNQ channel opener is analgesic in the hotplate test. Mice were dosed PO, one hour prior to testing. The mouse was placed on the plate with the temperature set at 55° C. When it licked its hind paw, or after 30 seconds, it was removed, and the latency to the lick was recorded. Doses of the KCNQ channel opener were 0, 10, 30, and 100 mg/kg.

One hour later the mouse was placed on a metal surface heated to 55° C. When the mouse licked its hind paw, or after 30 seconds, it was removed from the surface, and the latency to the lick was measured. The KCNQ opener compound increased the latency to lick a hind paw (see FIG. 5). When analyzed by analysis of variance, there was an overall significant effect of compound (p<0.001), with the 30 and 100 mg/kg doses significantly different from the vehicle. Both tests showed statistically significant differences between treated and untreated mice.

Example 6

In vivo Geller Conflict Test for Anxiolytics

In the Geller conflict test (see, e.g., Geller & Seifter, *Psychophamracologia* 1:482–492 (1960: Pollard & Howard, *Psychopharmacology* 62:117–121 (1979)), rats are trained to press a lever to receive food pellets during daily 1 hour sessions. The sessions are divided into punished and unpunished phases. During the four, three-minute punished periods, a light signals that each lever press will produce both a pellet and a foot shock (punishment), which reduces lever pressing. The number of punished lever presses on test days (when test compound is administered) is compared to the mean on baseline days. The positive control, chlordiazepoxide, increases punished lever pressing by >50%. A compound that produces an increase of approximately 40% or greater is generally considered to be of interest as a rapid-onset anxiolytic.

A compound with selective KCNQ2/3 channel opening activity increased punished responding in a dose-dependent manner (see FIG. 6). The increase in punished responding was statistically significant(paired t-test p<0.05) at 10, 17, 30, and 56 mg/kg PO with increases of 40% or greater at 30 and 56 mg/kg. Responding in the unpunished phase was not disrupted, indicating that the animals were not impaired at the doses tested.

What is claimed is:

1. A method for reducing pain in a subject in need thereof by increasing ion flow through KCNQ potassium channels in a cell, the method comprising the step of administering to the subject a pharmaceutical composition comprising a pharmaceutically acceptable carrier and a compound able to increase ion flow through KCNQ potassium channels, said composition administered to the subject in a potassium channel-opening amount, thereby reducing pain in the subject.

2. The method of claim 1, wherein the pain is somatic pain.
3. The method of claim 2, wherein the pain is cutaneous.
4. The method of claim 2, wherein the pain is visceral.
5. The method of claim 2, wherein the pain is caused by a burn, a bruise, an abrasion, a laceration, a broken bone, a torn ligament, a torn tendon, a torn muscle, a viral infection, a bacterial infection, a protozoal infection, a fungal infection, contact dermatitis, inflammation, or cancer.
6. The method of claim 5, wherein the inflammation is caused by trauma, infection, surgery, burns, or diseases with an inflammatory component.
7. The method of claim 1, wherein the pain is neuropathic.
8. The method of claim 7, wherein the neuropathic pain is caused by injury to the central or peripheral nervous system due to cancer, HIV infection, tissue trauma, infection, autoimmune disease, diabetes, arthritis, diabetic neuropathy, trigeminal neuralgia or drug administration.
9. The method of claim 1, wherein the subject is a human.
10. The method of claim 1, wherein the KCNQ channel is a heteromeric channel.
11. The method of claim 1, wherein the KCNQ channel is a homomeric channel.
12. The method of claim 10, wherein the heteromeric KCNQ channel comprises a KCNQ2 polypeptide subunit.
13. The method of claim 10, wherein the heteromeric KCNQ channel comprises a KCNQ3 polypeptide subunit.
14. The method of claim 12, wherein the KCNQ channel is KCNQ2/3.
15. The method of claim 1, wherein the potassium channel-opening amount is 0.1 mg/kg to 200 mg/kg.
16. The method of claim 15, wherein the potassium channel-opening amount is 10 mg/kg to 100 mg/kg.
17. The method of claim 1, wherein the composition is administered orally.
18. The method of claim 1, wherein the composition is administered by injection.
19. The method of claim 1, wherein the composition is administered after a surgical procedure.
20. The method of claim 1, wherein the compound able to increase ion flow through KCNQ potassium channels has the formula:

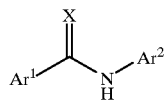

wherein
$Ar^1$ and $Ar^2$ are each members independently selected from the group consisting of aryl, substituted aryl, heteroaryl and substituted heteroaryl; and
X is a member selected from the group consisting of O, S and N—$R^1$,
wherein $R^1$ is a member selected from the group consisting of H, $(C_1-C_8)$alkyl, substituted $(C_1-C_8)$ alkyl, aryl, substituted aryl, heteroaryl, substituted heteroaryl, aryl$(C_1-C_4)$alkyl, substituted aryl $(C_1-C_4)$alkyl, CN, —C(O)$R^2$, —O$R^3$, —C(O) N$R^3R^4$, and —S(O)$_2$N$R^3R^4$;
wherein $R^2$ is a member selected from the group consisting of $(C_1-C_8)$alkyl, substituted $(C_1-C_8)$ alkyl, aryl, substituted aryl, heteroaryl, substituted heteroaryl, aryl$(C_1-C_4)$alkyl and substituted aryl $(C_1-C_4)$alkyl; and
$R^3$ and $R^4$ are each members independently selected from the group consisting of hydrogen, $(C_1-C_8)$alkyl, substituted $(C_1-C_8)$alkyl, aryl, substituted aryl, heteroaryl, substituted heteroaryl, aryl$(C_1-C_4)$alkyl and substituted aryl$(C_1-C_4)$alkyl, or $R^3$ and $R^4$ can be combined with the nitrogen to which each is attached to form a 5-, 6- or 7-membered ring optionally having additional heteroatoms at the ring vertices.

21. The method according to claim 20, wherein $Ar^1$ is a member selected from the group consisting of phenyl, substituted phenyl, indolyl, substituted indolyl, benzofuranyl, substituted benzofuranyl, furanyl, substituted furanyl, thienyl, substituted thienyl, isothiazolyl, substituted isothiazolyl, pyrazolyl and substituted pyrazolyl.
22. The method according to claim 20, wherein $Ar^1$ is substituted phenyl, substituted or unsubstituted 2-indolyl and substituted or unsubstituted 2-thienyl.
23. The method according to claim 20, wherein X is O.
24. The method according to claim 22, wherein the $Ar^1$ substituents are selected from the group consisting of halogen, alkyl, halo$(C_1-C_4)$alkyl, $(C_1-C_4)$alkoxy, halo $(C_1-C_4)$alkoxy, nitro, cyano, —NHC(O)$R^7$, —NH$R^7$, phenyl and substituted phenyl, wherein
$R^7$ is a member selected from hydrogen, $(C_1-C_8)$alkyl, substituted $(C_1-C_8)$alkyl, cycloalkyl, substituted cycloalkyl, heteroalkyl, substituted heteroalkyl, heterocyclyl, substituted heterocyclyl, aryl, substituted aryl, heteroaryl, substituted heteroaryl, aryl$(C_1-C_4)$ alkyl and substituted aryl$(C_1-C_4)$alkyl, or $R^7$ can be combined with the nitrogen to which it is attached to form a 5-, 6- or 7-membered ring optionally having additional heteroatoms at the ring vertices.
25. The method according to claim 20, wherein $Ar^2$ is selected from the group consisting of heteroaryl and substituted heteroaryl.
26. The method according to claim 20, wherein $Ar^1$ is substituted aryl; $Ar^2$ is heteroaryl or substituted heteroaryl; and X is O.
27. The method according to claim 24, wherein $Ar^2$ is pyridyl or substituted pyridyl.
28. The method according to claim 27, wherein $Ar^2$ is selected from the group consisting of 6-methyl-3-pyridyl and 2-chloro-5-pyridyl.
29. The method according to claim 27, wherein $Ar^1$ is substituted phenyl.
30. The method according to claim 29, said compound having the formula:

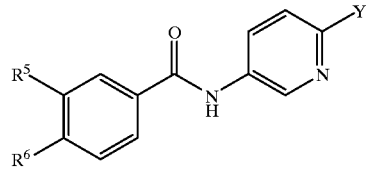

wherein,
Y is a member selected from the group consisting of halogen, $C_1-C_4$ alkyl, $C_1-C_4$ substituted alkyl, —OCH$_3$ and —OCF$_3$, and
$R^5$ and $R^6$ are members independently selected from the group consisting of H, halogen, alkyl, halo$(C_1-C_4)$ alkyl, nitro, cyano and phenyl, with the proviso that both $R^5$ and $R^6$ are not H.
31. The method according to claim 30, wherein $R^5$ and $R^6$ are members independently selected from the group consisting of H, F, and Cl, with the proviso that both $R^5$ and $R^6$ are not H.

* * * * *